United States Patent
Gopal et al.

(10) Patent No.: US 11,708,315 B2
(45) Date of Patent: Jul. 25, 2023

(54) METHOD OF PRETREATING ION-EXCHANGE RESIN FOR REMOVAL OF ALDEHYDE IMPURITIES

(71) Applicant: SABIC Global Technologies B.V., Bergen op Zoom (NL)

(72) Inventors: Srikant Gopal, Riyadh (SA); Adel Al-Dossari, Riyadh (SA); Jintang Duan, Riyadh (SA)

(73) Assignee: SABIC GLOBAL TECHNOLOGIES B.V., Bergen Op Zoom (NL)

( * ) Notice: Subject to any disclaimer, the term of this patent is extended or adjusted under 35 U.S.C. 154(b) by 0 days.

(21) Appl. No.: 17/914,677

(22) PCT Filed: Mar. 4, 2021

(86) PCT No.: PCT/IB2021/051837
§ 371 (c)(1),
(2) Date: Sep. 26, 2022

(87) PCT Pub. No.: WO2021/198806
PCT Pub. Date: Oct. 7, 2021

(65) Prior Publication Data
US 2023/0106288 A1    Apr. 6, 2023

Related U.S. Application Data

(60) Provisional application No. 63/002,216, filed on Mar. 30, 2020.

(51) Int. Cl.
| | |
|---|---|
| *C07C 29/76* | (2006.01) |
| *B01D 15/20* | (2006.01) |
| *B01J 47/016* | (2017.01) |
| *B01J 39/05* | (2017.01) |
| *B01D 15/36* | (2006.01) |
| *B01J 39/20* | (2006.01) |

(52) U.S. Cl.
CPC .............. *C07C 29/76* (2013.01); *B01D 15/20* (2013.01); *B01D 15/362* (2013.01); *B01J 39/05* (2017.01); *B01J 39/20* (2013.01); *B01J 47/016* (2017.01)

(58) Field of Classification Search
CPC ...... C07C 29/76; B01D 15/20; B01D 15/362; B01J 39/05; B01J 39/20; B01J 47/016
USPC ........................................................ 568/872
See application file for complete search history.

(56) References Cited

U.S. PATENT DOCUMENTS

2004/0211658 A1    10/2004    Sanderson et al.

FOREIGN PATENT DOCUMENTS

| CA | 1330350 C | 6/1994 |
|---|---|---|
| GB | 1219018 A | 1/1971 |

OTHER PUBLICATIONS

Foreign Communication from Related Application—International Search Report and Written Opinion of the International Searching Authority, International Application No. PCT/IB2021/051837, dated Jun. 7, 2021 10 pages.

*Primary Examiner* — Ana Z Muresan
(74) *Attorney, Agent, or Firm* — Norton Rose Fulbright US LLP

(57) ABSTRACT

Method for lowering aldehyde content in a mixture comprising (i) diethylene glycol (DEG) and/or triethylene glycol (TEG) and (ii) aldehyde are disclosed. An ion exchange resin is soaked in monoethylene glycol. The mixture comprising 5 to 200 ppm aldehyde is then flowed to make contact with the soaked ion exchange resin to produce a product comprising DEG and/or TEG and less than 15 ppm aldehyde.

20 Claims, 1 Drawing Sheet

METHOD OF PRETREATING ION-EXCHANGE RESIN FOR REMOVAL OF ALDEHYDE IMPURITIES

CROSS REFERENCE TO RELATED APPLICATIONS

This application is a filing under 35 U.S.C. 371 of International Application No. PCT/IB2021/051837 filed Mar. 4, 2021, entitled "Method of Pretreating Ion-Exchange Resin for Removal of Aldehyde Impurities," which claims priority to U.S. Provisional Application No. 63/002,216, filed Mar. 30, 2020, which applications are incorporated by reference herein in their entirety.

FIELD OF INVENTION

The present invention generally relates to systems and methods for reducing aldehyde levels in diethylene glycol and/or triethylene glycol. More specifically, the present invention relates to systems and methods for reducing aldehyde levels in diethylene glycol and/or triethylene glycol using monoethylene glycol soaked ion-exchange resins.

BACKGROUND OF THE INVENTION

Ethylene glycols, including monoethylene glycol, diethylene glycol, triethylene glycol, and polyethylene glycol, are a group of versatile chemicals used in many areas of the chemical industry. For instance, monoethylene glycol (MEG) is used as an antifreeze and coolant for engines and an intermediate for producing polyester fibers and polyethylene terephthalate (PET), which is used for producing plastic bottles. Diethylene glycol (DEG) can be used to produce polyurethanes, plasticizers, and organic solvents. Triethylene glycol (TEG) is often used as a plasticizer and moisture-retaining agent. Polyethylene glycol (PEG) is used in perfumes, cosmetics, lubricants, and plasticizers.

Generally, ethylene glycols, especially diethylene glycol and triethylene glycol, contain aldehyde as a contaminant due to various factors including oxidation of the ethylene glycols. Aldehyde can also be introduced into ethylene glycols from a reactor used for producing ethylene oxide, which is a reactant for producing ethylene glycols. One of methods commonly used to reduce the aldehyde content in ethylene glycols includes treating the ethylene glycol with a strong acidic cation exchange resin. In this method, the ion-exchange resin is first soaked in the target product (i.e., the ethylene glycol) for several hours for the resin to undergo swelling. The target product is then flowed through the soaked ion-exchange resin to remove the aldehyde. However, this method has been proven to be only highly effective for removing aldehyde content in monoethylene glycol. The performance of the strong acidic cation exchange resin in treating diethylene glycol and triethylene glycol is relatively poor.

Overall, while the methods of reducing aldehyde in ethylene glycols exist, the need for improvements in this field persists in light of at least the aforementioned drawbacks for the conventional methods

BRIEF SUMMARY OF THE INVENTION

A solution to at least some of the above-mentioned problems associated with the reduction of aldehyde content in a mixture comprising diethylene glycol and/or triethylene glycol has been discovered. The solution resides in a method of lowering aldehyde content in diethylene glycol and/or triethylene glycol using monoethylene glycol soaked ion-exchange resin. This method, in certain embodiments, avoids using diethylene glycol and/or triethylene glycol to soak the ion-exchange resin before treating the diethylene glycol and/or triethylene glycol. This can be beneficial for at least preventing reduction of efficiency of the ion-exchange resin caused by soaking in diethylene glycol and/or triethylene glycol. Thus, this method is capable of maintaining high efficiency of the ion-exchange resin for removing aldehyde. Therefore, the method of the present invention provides a technical solution to at least some of the problems associated with the conventional methods for reducing aldehyde content in ethylene glycols.

Embodiments of the invention include a method of lowering aldehyde content of a mixture comprising diethylene glycol (DEG) and 5 to 200 ppm aldehyde. The method comprises soaking ion-exchange resin in monoethylene glycol. The method further comprises contacting the soaked ion-exchange resin with the mixture to produce a product comprising DEG and less than 15 ppm aldehyde.

Embodiments of the invention include a method of lowering aldehyde content of a mixture comprising diethylene glycol (DEG) and 5 to 200 ppm aldehyde. The method comprises soaking ion-exchange resin in monoethylene glycol for at least 4 hours at a temperature of 0 to 60° C. The method further comprises contacting the soaked ion-exchange resin with the mixture to produce a product comprising DEG and less than 15 ppm aldehyde.

Embodiments of the invention include a method of lowering aldehyde content of a mixture comprising triethylene glycol (TEG) and 5 to 200 ppm aldehyde. The method comprises soaking ion-exchange resin in monoethylene glycol. The method further comprises contacting the soaked ion-exchange resin with the mixture to produce a product comprising TEG and less than 15 ppm aldehyde.

Embodiments of the invention include a method of lowering aldehyde content of a mixture comprising triethylene glycol (TEG) and 5 to 200 ppm aldehyde. The method comprises soaking ion-exchange resin in monoethylene glycol for at least 4 hours at a temperature of 0 to 60° C. The method further comprises contacting the soaked ion-exchange resin with the mixture to produce TEG comprising less than 15 ppm aldehyde.

The following includes definitions of various terms and phrases used throughout this specification.

The terms "about" or "approximately" are defined as being close to as understood by one of ordinary skill in the art. In one non-limiting embodiment the terms are defined to be within 10%, preferably, within 5%, more preferably, within 1%, and most preferably, within 0.5%.

The terms "wt. %", "vol. %" or "mol. %" refer to a weight, volume, or molar percentage of a component, respectively, based on the total weight, the total volume, or the total moles of material that includes the component. In a non-limiting example, 10 moles of component in 100 moles of the material is 10 mol. % of component.

The term "substantially" and its variations are defined to include ranges within 10%, within 5%, within 1%, or within 0.5%.

The terms "inhibiting" or "reducing" or "preventing" or "avoiding" or any variation of these terms, when used in the claims and/or the specification, include any measurable decrease or complete inhibition to achieve a desired result.

The term "effective," as that term is used in the specification and/or claims, means adequate to accomplish a desired, expected, or intended result.

The term "plural ethylene glycol," as that term is used in the specification and/or claims, means diethylene glycol or triethylene glycol.

The use of the words "a" or "an" when used in conjunction with the term "comprising," "including," "containing," or "having" in the claims or the specification may mean "one," but it is also consistent with the meaning of "one or more," "at least one," and "one or more than one."

The words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The process of the present invention can "comprise," "consist essentially of," or "consist of" particular ingredients, components, compositions, etc., disclosed throughout the specification.

The term "primarily," as that term is used in the specification and/or claims, means greater than any of 50 wt. %, 50 mol. %, and 50 vol. %. For example, "primarily" may include 50.1 wt. % to 100 wt. % and all values and ranges there between, 50.1 mol. % to 100 mol. % and all values and ranges there between, or 50.1 vol. % to 100 vol. % and all values and ranges there between.

Other objects, features and advantages of the present invention will become apparent from the following figures, detailed description, and examples. It should be understood, however, that the figures, detailed description, and examples, while indicating specific embodiments of the invention, are given by way of illustration only and are not meant to be limiting. Additionally, it is contemplated that changes and modifications within the spirit and scope of the invention will become apparent to those skilled in the art from this detailed description. In further embodiments, features from specific embodiments may be combined with features from other embodiments. For example, features from one embodiment may be combined with features from any of the other embodiments. In further embodiments, additional features may be added to the specific embodiments described herein.

BRIEF DESCRIPTION OF THE DRAWINGS

For a more complete understanding, reference is now made to the following descriptions taken in conjunction with the accompanying drawings, in which.

DETAILED DESCRIPTION OF THE INVENTION

Currently, available methods of reducing aldehyde level in diethylene glycol and/or triethylene glycol include soaking a strong acidic cation exchange resin with the target product (i.e., diethylene glycol and/or triethlyene glycol) and contacting the diethylene glycol and/or triethlyene glycol with the soaked cation exchange resin. However, this method can be inefficient because soaking the cation exchange resin with diethylene glycol and/or triethlyene glycol for several hours can be detrimental to the ability of the resin to reduce aldehyde content. The present invention provides a solution to this problem. The solution is premised on a method of lowering aldehyde content in diethylene glycol and/or triethlyene glycol by contacting the aldehyde containing diethylene glycol and/or triethlyene glycol with an ion-exchange resin that is soaked in monoethylene glycol. Thus, this method is capable of retaining the aldehyde removing/reducing/lowering ability for the ion-exchange resin before the diethylene glycol and/or triethylene glycol is treated for aldehyde removal, resulting in high aldehyde lowering efficiency. These and other non-limiting aspects of the present invention are discussed in further detail in the following sections.

A. System for Reducing Aldehyde Content in DEG and/or TEG

Figure 1:
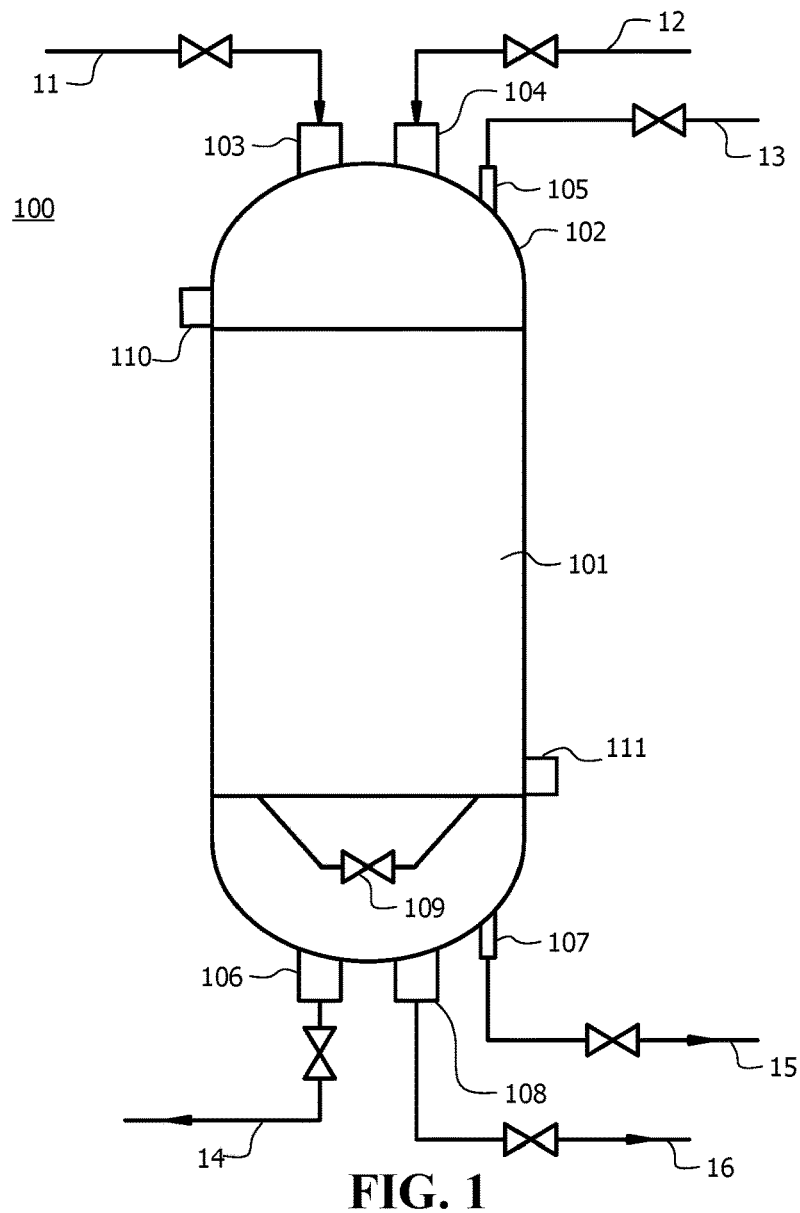
FIG. 1 shows a schematic diagram for a system of reducing aldehyde content in a mixture comprising aldehyde and diethylene glycol and/or triethylene glycol, according to embodiments of the invention.

In embodiments of the invention, the system for lowering aldehyde in DEG and/or TEG can include a bed of an ion-exchange resin, and a shell for containing the bed. With reference to FIG. 1, a schematic diagram is shown of system 100 for reducing aldehyde content in DEG and/or TEG. According to embodiments of the invention, system 100 includes bed 101 of an ion-exchange resin.

In embodiments of the invention, the ion-exchange resin is configured to remove aldehyde from diethylene glycol and/or triethylene glycol. According to embodiments of the invention, the ion-exchange resin includes crosslinked polystyrene, polystyrene crosslinked with divinylbenzene, or combinations thereof. In embodiments of the invention, the ion-exchange resin is an acid resin, preferably a strong acid resin including resins with sulfonic acid functional groups. The ion exchange resin may include strong acidic cation exchange resin. Non-limiting examples of the strong acidic cation exchange resin include sodium polystyrene sulfonate, poly(2-acrylamido-2-methyl-1-propanesulfonic acid), or combinations thereof.

According to embodiments of the invention, bed 101 comprises the ion-exchange resin in the form of beads. In embodiments of the invention, the beads of bed 101 have an average size of 0.3 to 1.5 mm and all ranges and values there between including ranges of 0.3 to 0.6 mm, 0.6 to 0.9 mm, 0.9 to 1.2 mm, and 1.2 to 1.5 mm. The beads of bed 101 may be macroporous with an average pore size greater than 50 Å.

In embodiments of the invention, bed 101 may be disposed in shell 102. According to embodiments of the invention, shell 102 may include a column. Shell 102 may be made of a material comprising stainless steel. In embodiments of the invention, the column has a length to diameter ratio in a range of 0.5 to 5 and all ranges and values there between including ranges of 0.5 to 1.0, 1.0 to 1.5, 1.5 to 2.0, 2.0 to 2.5, 2.5 to 3.0, 3.0 to 3.5, 3.5 to 4.0, 4.0 to 4.5, and 4.5 to 5.0. In embodiments of the invention, bed 101 occupies about 50 to 80% of the volume of shell 102 and all ranges and values there between.

In embodiments of the invention, system 100 includes inlet 103 disposed on an end of shell 102, configured to receive feed stream 11 into shell 102. In embodiments of the invention, inlet 103 is further configured to load resin into shell 102. In addition to, or as an alternative to inlet 103, system 100 may include a separate resin loading inlet configured to receive resin in shell 102. According to embodiments of the invention, inlet 103 may be further configured to receive soaking medium stream 12 into shell 102. Soaking medium stream 12 may include monoethylene glycol. In embodiments of invention, soaking medium stream 12 includes less than 10 ppm aldehyde. In embodiments of the invention, inlet 103 may be further still configured to receive inert gas stream 13 into shell 102. Inert gas stream may include nitrogen.

As an alternative or in addition to inlet 103 for receiving soaking medium stream 12, system 100 may include soaking medium inlet 104 disposed on shell 102, configured to receive soaking medium stream 12 into shell 102. As an alternative or in addition to inlet 103 for receiving inert gas stream 13, system 100 may include gas inlet 105 disposed on shell 102, configured to receive inert gas stream 13 into shell 102.

In certain embodiments of the invention, system 100 includes outlet 106 disposed on the end of shell 102 that is opposite to inlet 103. According to certain embodiments of invention, outlet 106 may be configured to release one or more of product stream 14, exiting gas stream 15, and spent soaking medium stream 16 from shell 102. In certain embodiments of the invention, system 100 may include outlet 106, gas outlet 107, and soaking medium outlet 108 configured to release product stream 14, exiting gas stream 15, and spent soaking medium stream 16 from shell 102, respectively.

According to certain embodiments of the invention, system 100 may include resin trap 109 disposed downstream to bed 101. Resin trap 109 may be configured to substantially prevent ion-exchange resin from inadvertently exiting shell 102. In certain embodiments of the invention, resin trap 109 can be disposed inside or outside of shell 102. According to certain embodiments of the invention, system 100 may further include resin inlet 110 and resin outlet 111 configured to receive the ion-exchange resin into shell 102 and release the ion-exchange resin from shell 102, respectively.

B Method of Reducing Aldehyde Content in DEG and/or TEG

Figure 2:
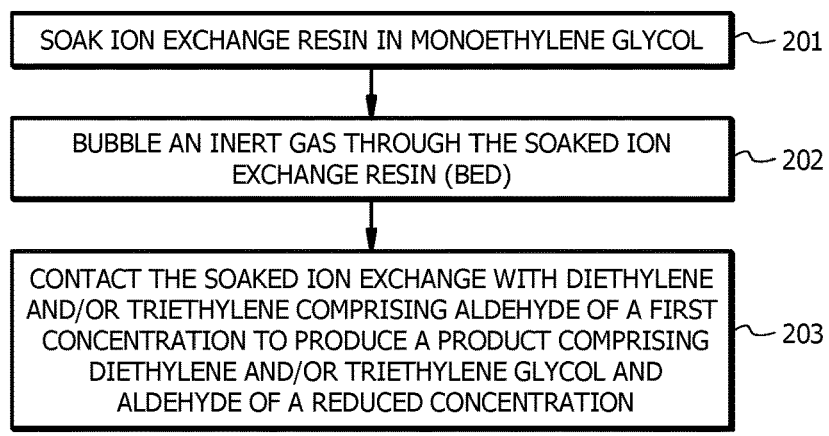
FIG. 2 shows a schematic flowchart for a method of reducing aldehyde content in a mixture comprising aldehyde and diethylene glycol and/or triethylene glycol, according to embodiments of the invention.

Methods of lowering aldehyde content in diethylene glycol and/or triethylene glycol using ion-exchange resin have been discovered. Certain embodiments of the method are capable of improving the efficiency of ion-exchange resin for reducing aldehyde content in DEG and/or TEG compared to conventional methods. As shown in FIG. 2, certain embodiments of the invention include method 200 for lowering aldehyde content in a mixture comprising (i) diethylene glycol and/or triethylene glycol and (ii) aldehyde. Method 200 may be implemented by system 100, as shown in FIG. 1.

According to certain embodiments of the invention, as shown in block 201, method 200 includes soaking ion-exchange resin in monoethylene glycol. In certain embodiments of the invention, the ion-exchange resin is packed as bed 101. In certain embodiments of the invention, the monoethylene glycol contains 0 to 10 ppm of aldehyde and all ranges and values there between including ranges of 0 to 0.5 ppm, 0.5 to 1.0 ppm, 1.0 to 1.5 ppm, 1.5 to 2.0 ppm, 2.0 to 2.5 ppm, 2.5 to 3.0 ppm, 3.0 to 3.5 ppm, 3.5 to 4.0 ppm, 4.0 to 4.5 ppm, 4.5 to 5.0 ppm, 5.0 to 5.5 ppm, 5.5 to 6.0 ppm, 6.0 to 6.5 ppm, 6.5 to 7.0 ppm, 7.0 to 7.5 ppm, 7.5 to 8.0 ppm, 8.0 to 8.5 ppm, 8.5 to 9.0 ppm, 9.0 to 9.5 ppm, and 9.5 to 10 ppm. In certain embodiments of the invention, the monoethylene glycol comprises fiber grade monoethylene glycol.

According to certain embodiments of the invention, at block 201, the ion-exchange resin is soaked for at least 4 hours, preferably more than 6 hours. In certain embodiments of the invention, prior to the soaking step at block 201, ion-exchange resin may have contained up to 60 wt. % water. According to embodiments of the invention, at block 201, during soaking, ion-exchange resin is capable of expanding to a volume that is 1 to 3 times of the volume before the ion-exchange resin is soaked. In embodiments of the invention, the soaking at block 201 is carried out at a temperature of 0 to 60° C. and all ranges and values there between including ranges of 0 to 3° C., 3 to 6° C., 6 to 9° C., 9 to 12° C., 12 to 15° C., 15 to 18° C., 18 to 21° C., 21 to 24° C., 24 to 27° C., 27 to 30° C., 30 to 33° C., 33 to 36° C., 36 to 39° C., 39 to 42° C., 42 to 45° C., 45 to 48° C., 48 to 51° C., 51 to 54° C., 54 to 57° C., and 57 to 60° C. According to certain embodiments of the invention, bed 101 is further flushed with monoethylene glycol.

According to certain embodiments of the invention, as shown in block 202, method 200 includes bubbling an inert gas through bed 101 of the ion exchange resin. In certain embodiments of the invention, the bubbling at block 202 is configured to remove fine particles from the ion exchange resin of bed 101. Bubbling at block 202 may be further configured to ensure proper packing, which entails sufficient contact between resin and the fluid such that the fluid does not bypass part of the resin bed of bed 101. In certain embodiments of the invention, the inert gas includes nitrogen. In certain embodiments of the invention, at block 202, the inert gas is bubbled through bed 101 at a flowrate such that a light fluidization of resin is developed. The bubbling at block 202 may be carried out at a temperature of 0 to 60° C. and all ranges and values there between including ranges of 0 to 3° C., 3 to 6° C., 6 to 9° C., 9 to 12° C., 12 to 15° C., 15 to 18° C., 18 to 21° C., 21 to 24° C., 24 to 27° C., 27 to 30° C., 30 to 33° C., 33 to 36° C., 36 to 39° C., 39 to 42° C., 42 to 45° C., 45 to 48° C., 48 to 51° C., 51 to 54° C., 54 to 57° C., and 57 to 60° C.

According to certain embodiments of the invention, as shown in block 203, method 200 includes contacting the soaked ion exchange resin with the mixture to produce a product comprising (i) diethylene or triethylene glycol and (ii) aldehyde with a concentration lower than the aldehyde concentration in the mixture.

In certain embodiments of the invention, the mixture comprises 5 to 200 ppm aldehyde and all ranges and values there between including 5 to 10 ppm, 10 to 20 ppm, 20 to 30 ppm, 30 to 40 ppm, 40 to 50 ppm, 50 to 60 ppm, 60 to 70 ppm, 70 to 80 ppm, 80 to 90 ppm, 90 to 100 ppm, 100 to 110 ppm, 110 to 120 ppm, 120 to 130 ppm, 130 to 140 ppm, 140 to 150 ppm, 150 to 160 ppm, 160 to 170 ppm, 170 to 180 ppm, 180 to 190 ppm, and 190 to 200 ppm. The product comprises 0 to 15 ppm aldehyde and all ranges and values there between including ranges of 0 to 1 ppm, 1 to 2 ppm, 2 to 3 ppm, 3 to 4 ppm, 4 to 5 ppm, 5 to 6 ppm, 6 to 7 ppm, 7 to 8 ppm, 8 to 9 ppm, 9 to 10 ppm, 10 to 11 ppm, 11 to 12 ppm, 12 to 13 ppm, 13 to 14 ppm, and 14 to 15 ppm.

In certain embodiments of the invention, the contacting is carried out at a temperature of 0 to 65° C. and all ranges and values there between including ranges of 0 to 3° C., 3 to 6° C., 6 to 9° C., 9 to 12° C., 12 to 15° C., 15 to 18° C., 18 to 21° C., 21 to 24° C., 24 to 27° C., 27 to 30° C., 30 to 33° C., 33 to 36° C., 36 to 39° C., 39 to 42° C., 42 to 45° C., 45 to 48° C., 48 to 51° C., 51 to 54° C., 54 to 57° C., 57 to 60° C., 60 to 63° C., and 63 to 65° C. According to certain embodiments of the invention, the contacting at block 203 including flowing the DEG and/or TEG through bed 101 of ion-exchange resin. In certain embodiments of the invention, at block 203, the DEG and/or TEG is flowed through the ion-exchanger resin at a flow rate of 0.1 to 10 bed volumes per hour (a liquid hourly space velocity of 0.1 to 10 hr$^{-1}$) and all ranges and values there between including 0.1 to 0.2 hr$^{-1}$, 0.2 to 0.3 hr$^{-1}$, 0.3 to 0.4 hr$^{-1}$, 0.4 to 0.5 hr$^{-1}$, 0.5 to 0.6 hr$^{-1}$, 0.6 to 0.7 hr$^{-1}$, 0.7 to 0.8 hr$^{-1}$, 0.8 to 0.9 hr$^{-1}$, 0.9 to 1 hr$^{-1}$, 1 to 2 hr$^{-1}$, 2 to 3 hr$^{-1}$, 3 to 4 hr$^{-1}$, 4 to 5 hr$^{-1}$, 5 to 6 hr$^{-1}$, 6 to 7 hr$^{-1}$, 7 to 8 hr$^{-1}$, 8 to 9 hr$^{-1}$, and 9 to 10 hr$^{1}$.

In certain embodiments of the invention, method 200 may further include back-flushing the product produced at block 203 in a direction opposite to the DEG and/or TEG flow direction at block 203. Back-flushing may be further conducted during start-up of method 200, after soaking step at block 201 when contacting with the product is started. Back-flushing may further be performed periodically (e.g., every 2-4 months) during the whole process of method 200. The back flushing may be configured to further remove empty pockets in bed 101. In certain embodiments of the invention, the back flushing is carried out for less than 2 hours. According to certain embodiments of the invention, method 200 is a continuous process.

Although embodiments of the present invention have been described with reference to blocks of FIG. 2, it should be appreciated that operation of the present invention is not limited to the particular blocks and/or the particular order of the blocks illustrated in FIG. 2. Accordingly, various embodiments of the invention may provide functionality as described herein using various blocks in a sequence different than that of FIG. 2.

In the context of the present invention, at least the following 16 embodiments are described. Embodiment 1 is a method of lowering aldehyde content of a mixture containing (i) a plural ethylene glycol, wherein the plural ethylene glycol is diethylene glycol (DEG) or triethylene glycol (TEG), and (ii) 5 to 200 ppm aldehyde. The method includes soaking ion-exchange resin in monoethylene glycol. The method further includes contacting the soaked ion-exchange resin with the mixture containing the plural ethylene glycol and 5 to 200 ppm aldehyde to produce a product containing the plural ethylene glycol and less than 15 ppm aldehyde. Embodiment 2 is the method of embodiment 1, wherein the ion-exchange resin is soaked in monoethylene glycol for at least 4 hours. Embodiment 3 is the method of either of embodiments 1 or 2, wherein the ion-exchange resin is soaked in monoethylene glycol at a temperature of 0 to 60° C. Embodiment 4 is the method of any of embodiments 1 to 3, wherein the ion-exchange resin is acidic. Embodiment 5 is the method of any of embodiments 1 to 4, wherein the product contains 10 ppm or less aldehyde. Embodiment 6 is the method of any of embodiments 1 to 5, wherein the ion-exchange resin is packed in a bed. Embodiment 7 is the method of embodiment 6, wherein in the contacting step, the mixture is flowed through the ion-exchanger resin at a flow rate of 0.1 to 10 bed volumes per hour. Embodiment 8 is the method of either of embodiments 6 or 7, further including, prior to the contacting step, bubbling an inert gas through the bed of ion-exchange resin, and back-flushing the bed with the product. Embodiment 9 is the method of embodiment 8, wherein the steps of bubbling the inert gas and back-flushing are adapted to remove fine particles from the bed and/or ensure proper packing of the bed. Embodiment 10 is the method of either of embodiments 8 or 9, wherein the inert gas includes nitrogen. Embodiment 11 is the method of any of embodiments 8 to 10, wherein the back-flushing is carried out for less than 2 hours. Embodiment 12 is the method of any of embodiments 8 to 11, further including, prior to the back-flushing step, flushing the bed of ion-exchange resin with monoethylene glycol. Embodiment 13 is the method of any of embodiments 1 to 12, wherein the monoethylene glycol is in a mixture that contains less than 10 ppm aldehyde. Embodiment 14 is the method of any of embodiments 1 to 13, wherein the method is a continuous process. Embodiment 15 is the method of any of embodiments 1 to 14, wherein the contacting step is carried out at a temperature of 0 to 65° C. Embodiment 16 is the method of any of embodiments 1 to 15, wherein the monoethylene glycol is fiber grade monoethylene glycol.

Although embodiments of the present application and their advantages have been described in detail, it should be understood that various changes, substitutions and alterations can be made herein without departing from the spirit and scope of the embodiments as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the above disclosure, processes, machines, manufacture, compositions of matter, means, methods, or steps, presently existing or later to be developed that perform substantially the same function or achieve substantially the same result as the corresponding embodiments described herein may be utilized. Accordingly, the appended claims are intended to include within their scope such processes, machines, manufacture, compositions of matter, means, methods, or steps.

The invention claimed is:

1. A method of lowering aldehyde content of a mixture comprising (i) a plural ethylene glycol, wherein the plural ethylene glycol is diethylene glycol (DEG) or triethylene glycol (TEG), and (ii) 5 to 200 ppm aldehyde, the method comprising:
    soaking ion-exchange resin in monoethylene glycol; and
    contacting the soaked ion-exchange resin with the mixture comprising the plural ethylene glycol and 5 to 200 ppm aldehyde to produce a product comprising the plural ethylene glycol and less than 15 ppm aldehyde.

2. The method of claim 1, wherein the ion-exchange resin is soaked in monoethylene glycol for at least 4 hours.

3. The method of claim 1, wherein the ion-exchange resin is soaked in monoethylene glycol at a temperature of 0 to 60° C.

4. The method of claim 1, wherein the ion- exchange resin is acidic.

5. The method of claim 1, wherein the product contains 10 ppm or less aldehyde.

6. The method of claim 1, wherein the ion-exchange resin is packed in a bed.

7. The method of claim 6, wherein in the contacting step, the mixture is flowed through the ion-exchange resin at a flow rate of 0.1 to 10 bed volumes per hour.

8. The method of claim 6, further comprising:
    prior to the contacting step, bubbling an inert gas through the bed of ion-exchange resin; and
    back-flushing the bed with the product.

9. The method of claim 8, wherein the steps of bubbling the inert gas and back-flushing are adapted to remove fine particles from the bed and/or ensure proper packing of the bed.

10. The method of claim 8, wherein the inert gas comprises nitrogen.

11. The method of claim 8, wherein the back-flushing is carried out for less than 2 hours.

12. The method of claim 8, further comprising prior to the back-flushing step, flushing the bed of ion-exchange resin with monoethylene glycol.

13. The method of claim 1, wherein the monoethylene glycol is in a mixture that contains less than 10 ppm aldehyde.

14. The method of claim 1, wherein the method is a continuous process.

15. The method of claim 1, wherein the contacting step is carried out at a temperature of 0 to 65° C.

16. The method of wherein the monoethylene glycol is fiber grade monoethylene glycol.

17. The method of claim 3, wherein the monoethylene glycol is fiber grade monoethylene glycol.

18. The method of claim 4, wherein the monoethylene glycol is fiber grade monoethylene glycol.

19. The method of claim 5, wherein the monoethylene glycol is fiber grade monoethylene glycol.

20. The method of claim 6, wherein the monoethylene glycol is fiber grade monoethylene glycol.

\* \* \* \* \*

UNITED STATES PATENT AND TRADEMARK OFFICE
CERTIFICATE OF CORRECTION

| | | |
|---|---|---|
| PATENT NO. | : 11,708,315 B2 | |
| APPLICATION NO. | : 17/914677 | |
| DATED | : July 25, 2023 | |
| INVENTOR(S) | : Srikant Gopal et al. | |

It is certified that error appears in the above-identified patent and that said Letters Patent is hereby corrected as shown below:

In the Claims

In Claim 16, Column 9, Line 5, add --claim 1,-- after "method of".

Signed and Sealed this
Twelfth Day of September, 2023

Katherine Kelly Vidal
*Director of the United States Patent and Trademark Office*